United States Patent [19]

Bezwada et al.

[11] Patent Number: 5,371,176
[45] Date of Patent: Dec. 6, 1994

[54] CASTOR OIL POLYMERS

[75] Inventors: Rao S. Bezwada, Whitehouse Station; Alastair W. Hunter, Bridgewater; Walter McGregor, Flemington; Semyon Shchervinsky, Whitehouse Station, all of N.J.

[73] Assignee: Ethicon, Inc., Somerville, N.J.

[21] Appl. No.: 142,529

[22] Filed: Oct. 22, 1993

Related U.S. Application Data

[63] Continuation-in-part of Ser. No. 13,858, Feb. 5, 1993, abandoned, and a continuation-in-part of Ser. No. 15,706, Feb. 9, 1993, abandoned.

[51] Int. Cl.$^5$ .............................................. C08G 63/08
[52] U.S. Cl. ................................. 528/354; 528/355; 606/231
[58] Field of Search ................. 528/354, 355; 606/231

[56] References Cited

U.S. PATENT DOCUMENTS

| | | | |
|---|---|---|---|
| 3,461,093 | 8/1969 | Walton et al. | 524/512 |
| 4,027,676 | 6/1977 | Mattei | 606/231 |
| 4,153,776 | 5/1979 | Friedlander | 528/49 |
| 4,439,420 | 3/1984 | Mattei et al. | 424/78 |
| 4,443,430 | 4/1984 | Mattei | 424/78 |
| 4,624,256 | 11/1986 | Messler et al. | 128/335.5 |
| 4,650,665 | 3/1987 | Kronenthal et al. | 424/435 |
| 4,788,979 | 12/1988 | Jarrett et al. | 128/335.5 |
| 4,804,691 | 2/1989 | English et al. | 523/118 |
| 4,829,099 | 5/1989 | Fuller et al. | 523/111 |
| 4,994,074 | 2/1991 | Bezwada et al. | 606/230 |
| 5,007,923 | 4/1991 | Bezwada et al. | 606/231 |
| 5,019,094 | 5/1991 | Bezwada et al. | 606/230 |
| 5,037,950 | 8/1991 | Bezwada et al. | 528/354 |
| 5,047,048 | 9/1991 | Bezwada et al. | 606/231 |
| 5,076,807 | 12/1991 | Bezwada et al. | 606/230 |
| 5,104,390 | 4/1992 | Yum et al. | 604/323 |
| 5,115,035 | 5/1992 | Shiraki et al. | 525/314 |
| 5,123,912 | 6/1992 | Kaplan et al. | 606/230 |
| 5,129,889 | 7/1992 | Hahn et al. | 604/265 |
| 5,133,739 | 7/1992 | Bezwada et al. | 606/230 |
| 5,216,043 | 1/1993 | Sipinen et al. | 523/126 |

FOREIGN PATENT DOCUMENTS

| | | |
|---|---|---|
| 1260488 | 8/1989 | Canada . |
| 2055717 | 7/1977 | Japan . |

*Primary Examiner*—John Kight, III
*Assistant Examiner*—Terressa Mosley
*Attorney, Agent, or Firm*—Hal Brent Woodrow

[57] ABSTRACT

A polymer, particularly a biomedical polymer for the fabrication of medical and surgical devices and for use as a coating, is described. The polymer is derived from the reaction product of one or more lactone monomers and castor oil preferably: (a) ε-caprolactone, trimethylene carbonate or an ether lactone; (b) castor oil; and (c) glycolide, lactide or 1,4-dioxanone. The preferred polymer is derived from ε-caprolactone, castor oil, and glycolide.

The polymer in preferred embodiments is ideally suited for use as a coating for a surgical suture, particularly an absorbable, braided multifilament suture and surgical needles. For this application, glycerol is advantageously added to the reactive monomer mix from which the polymer is derived.

36 Claims, No Drawings

CASTOR OIL POLYMERS

This is a continuation-in-part of Ser. No. 08/013,858, filed Feb. 5, 1993, now abandoned and 08/015,706 filed Feb. 9, 1993 now abandoned both of which are hereby incorporated by reference.

BACKGROUND OF THE INVENTION

This invention relates to polymers which incorporate castor oil as a copolymerizable component. More specifically, it relates to such polymers having properties ideally adapted for biomedical applications particularly for the fabrication of surgical articles and coatings for surgical articles.

The need to develop suitable coatings for numerous applications, particularly surgical applications, continues unabated. A coating on the surface of a surgical article is often essential for the proper performance of the article. For example, surgical needles typically require that the surface of the needle be coated to reduce the penetration force of the needle when it is passed through tissue. The conventional coating which has been used to coat the surfaces of needles for many years is silicone, which is not bioabsorbable. Another example are surgical sutures. Surgical sutures often require coated surfaces to improve the ease with which the surgeon can run a knot down the suture to anchor the suture at the site of surgical trauma.

Additionally, the development of biomedical polymers for the fabrication of surgical articles, devices and coatings, has emerged as an area of particular emphasis in the advancement and improvement in the medical and surgical arts. Much work has been documented on the increasing use of polymers in the medical profession. These polymers exhibit a wide range of physical and biological properties for numerous applications.

One of the driving forces behind the development of medical-grade polymers is the need to replace metallic components of various biomedical devices, which must often be removed from the body following surgery, with bioabsorbable polymers that need not be removed from the body following surgery. However, the requirements for suitable polymer replacements of metallic components are quite strenuous—the polymer must come close to or match the physical properties of the substituted metal.

By far, the most widely used polymers for medical applications are those derived from lactone monomers. Correspondingly, a wealth of research has arisen to create novel polymer systems derived from new lactone monomer compositions. This has lead to the development of lactone-based polymers with a wide range of properties for different applications. See, for example, U.S. Pat. Nos. 4,624,256; 4,788,979; 4,994,074; 5,007,923; 5,019,094; 5,037,950; 5,047,048; 5,076,807; and 5,133,739.

Another component which is used in making polymers, although not widely used for making biomedical polymers, is castor oil. Castor oil is known as a lubricating oil, and therefore has found wide-spread use for coating applications. See, for example, U.S. Pat. No. 3,461,093, which describes a copolymer of castor oil and a mixture of ethylenically unsaturated monomers, such as α-methylstyrene and a hydroxyalkyl methacrylate. In addition, there have been limited reports of the use of castor oil to prepare polymers for medical and surgical applications. In this regard, Canadian Patent 1,260,488 describes copolymers of a predominant amount of glycolide or lactide (or a mixture of these), and castor oil. The copolymers are said to have a wax-like consistency, and therefore are ideally suited for use in bone wax formulations for the control of bleeding from cut bone surfaces. It is also known to use castor oil as an initiator in the bulk polymerization of lactone monomers, e.g. glycolide, to prepare monofilament surgical threads. Similarly, Japanese Patent 2,055,717 describes the use of an emulsion containing a castor oil component as a lubricant oil for thermoplastic filaments.

While the polymer systems described above all provide particular properties for well-targeted applications, a need still exists to develop biomedical polymers which have enhanced lubricity and pliability for numerous applications, particularly for the preparation of polymer coatings for the surface of surgical articles. This increase in lubricity would be especially worthy if it could be obtained without sacrificing the processability of the polymer for making surgical articles or coatings for such articles. Finally, these goals would be further enhanced if they could be achieved with a polymer which is bioabsorbable, and therefore could truly be considered a suitable replacement for metallic components in numerous surgical devices.

SUMMARY OF THE INVENTION

In one embodiment of this invention there is provided a bioabsorbable copolymer comprising the reaction product of a predominant amount of a lactone monomer and castor oil.

In a preferred embodiment of this invention there is provided a polymer comprises the reaction product of the following components: (a) $\epsilon$-caprolactone, trimethylene carbonate or an ether lactone; (b) castor oil; and (c) glycolide, lactide or 1,4-dioxanone.

The polymers of this invention are biocompatible, and therefore it can be used for numerous medical and surgical applications. The polymer exhibits improved lubricity and pliability in relation to polymers derived from conventional lactone monomer systems described in the art. The increased lubricity is obtained from the incorporation of castor oil as a reactive comonomer component in the polymer.

Surprisingly, incorporating $\epsilon$-caprolactone, trimethylene carbonate or an ether lactone, as a coreactive monomeric component with castor oil and glycolide, lactide or 1,4-dioxanone, increases the compatibility of the polymer reaction product in conventional organic solvents. This is important because the solubility the polymer in conventional solvents is necessary to readily make numerous surgical articles, and to apply the polymer to the surface of surgical articles as a coating to improve lubricity. In contrast to the bone wax formulations of the prior art which are derived from glycolide or lactide and castor oil, the polymer of this invention can be conveniently processed for numerous medical and surgical applications.

In the preferred embodiment, the polymer of this invention is bioabsorbable. This further broadens the utility of the polymer for many applications where bioabsorbability is a critical factor. For example, absorbable multifilament sutures are desirably coated with absorbable coatings so that no foreign matter remains intact within the body when the suture is left behind following surgery.

In another preferred embodiment, when the surgical article is a needle, the coated copolymer provides the needle with a significantly reduced penetration force relative to an uncoated needle. The penetration force is a measure of the ease with which the surgeon can pass the needle through the tissue and represents a truly important design parameter for the development of improved surgical needles. The penetration force of the surgical needles of this invention is comparable to that of needles coated with silicone and other conventional coatings.

The polymer of this invention may be used for any application which can benefit from its wide array of properties. Ideally, the polymer is especially adapted for medical and surgical applications, particularly for the fabrication of surgical articles or devices, and as coating polymers for surgical articles and devices.

DETAILED DESCRIPTION OF THE INVENTION

In one embodiment of the present invention a copolymer comprising predominately lactone repeating units with the remaining repeating units being castor oil are provided. Lactone monomers have been described in the art, for example in Polymer, 1979, Vol. 20, 1459–1464 by Gilding and Reed. Examples of lactone monomers include monomers selected from the group consisting of glycolide, lactide, 1,4-dioxanone, trimethylene carbonate, δ-valerolactone, ε-caprolactone, 1,4-dioxepan-2-one, 1,5-dioxepan-2-one, substituted equivalents of these compounds, cyclic dimers of these compounds and combinations of two or more thereof. The preferred lactone monomers are ε-caprolactone, 1,4-dioxanone, trimethylene carbonate, glycolide and lactide. The most preferred lactone monomers are ε-caprolactone, 1,4-dioxanone and glycolide.

For the purpose of describing this invention, a "predominate amount" of a lactone monomer refers to greater than or equal to about 50 percent by weight of lactone monomer based on the total weight of the reactive components which polymerize to form the coating copolymer. Generally, the amount of lactone monomer can be in the range of from about 50 to about 95 percent by weight. Preferably, the lactone monomer is present in an amount ranging from about 70 to about 90 percent by weight. The most preferred range is between about 80 to about 90 percent by weight. If the amount of lactone monomer were substantially less than 50 percent by weight, then the viscosity of the resulting copolymer would decrease below acceptable levels for ideal film-forming properties in the preparation of coating copolymers. Alternatively, if the amount of lactone monomer were greater than about 95 percent by weight of the reactive mixture, then the increased lubricity which the castor oil provides would be undesirably diminished.

In another embodiment of the present invention mixtures of lactone monomers are used. The preferred polymer comprises the reaction product of the following components: (a) ε-caprolactone, trimethylene carbonate or an ether lactone; (b) castor oil; and (c) glycolide, lactide or 1,4-dioxanone. For the purpose of describing this invention, an "ether lactone" is 1,4-dioxepan-2-one, 1,5-dioxepan-2-one, and substituted equivalents of these compounds as well as the cyclic dimers of these compounds.

To simplify the description of this invention, the monomeric component of the polymer which may be any of ε-caprolactone, trimethylene carbonate or an ether lactone, will be referred to as the "soft monomer". The polymerization of any of the soft monomers alone would be generally characterized by a final polymer product which has a glass transition temperature below room temperature, and a soft feel. Conversely, the monomeric component which may be any of glycolide, lactone, or 1,4-dioxanone, will be referred to as the "hard monomer". Polymers derived from the hard monomers alone would typically be relatively more stiff than those derived from the soft monomers. Included within the scope of soft and hard monomers are mixtures of soft monomers and mixtures of hard monomers. For example, the soft monomer may actually be a mixture of ε-caprolactone and trimethylene carbonate, and the hard monomer may be a mixture of glycolide and lactide.

The most preferred soft monomer is ε-caprolactone, and the preferred hard monomer is glycolide. Therefore, the preferred polymer is a polymer derived from the reaction of ε-caprolactone, castor oil and glycolide.

Castor oil is a well known material, and is described, for example, in Encyclopedia of Chemical Technology, Volume 5, John Wiley & Sons (1979). The preferred castor oil is a medical grade, United States Pharmacopeia (USP) castor oil.

The amount of the soft monomer based on the weight of the reactive components in the mixture from which the polymer is derived preferably ranges from about 10 to about 90 parts by weight, more preferably from about 20 to about 80 parts by weight and most preferably from in the range of about 50 to about 85 parts by weight for needle coatings. If the amount of soft monomer is less than about 10 parts by weight, then the resulting polymer may be incompatible with conventional solvents, thus rendering the polymer unsuitable for numerous applications. In addition, the stiffness may be higher than desired for numerous applications, particularly when the polymer is used as a coating polymer. If the amount of the soft monomer were greater than about 90 parts by weight, then the rate of absorption in bodily tissue may be too slow for numerous medical and surgical applications.

The amount of the castor oil component in the reactive mixture from which the polymer is derived preferably ranges from about 5 to about 60 parts by weight, more preferably from about 10 to about 50 parts by weight. If the amount of castor oil were less than about 10 parts by weight, then the lubricity and pliability of the polymer may be diminished, which is particularly significant for coating applications. If the amount of castor oil were greater than about 60 parts by weight, then the resulting viscosity of the polymer may be too low for acceptable film-forming properties, which are critical for the preparation of coatings or devices in the medical industry.

The hard monomer concentration is preferably between about 90 to about 10 parts by weight of the co-reactive components in the mixture, more preferably about 80 to about 20 parts by weight. If the amount of hard monomer were less than about 10 parts by weight, then the rate of absorption may be too slow. If the amount of hard monomer were greater than about 90 parts by weight, then the polymer may be difficult to process because of its potential incompatibility with solvents, and its properties for coating applications may also diminish.

It may be desirable to add additional ingredients to the reactive monomer mixture from which the polymer is derived, to further enhance desired properties for particular applications. In a particularly preferred embodiment, glycerol is added to the monomer mix, and therefore the polymer comprises the reaction product of not only the soft and hard monomer components with castor oil, but also glycerol. Glycerol may further enhance the lubricity of the resulting polymer, a property which is especially desired for coating applications. The amount of glycerol in the monomer mix is preferably in the range of from about 0.5 to about 30 parts by weight, more preferably in the range of from about 5 to about 15 parts by weight for coating sutures and in the range of from about 1 to about 5 parts by weight for coating needles. If the amount of glycerol were greater than about 30 parts by weight, than the viscosity of the resulting polymer may decrease undesirably to the point where it would lack the bulk properties so necessary for numerous applications, particularly coating applications.

The polymer of this invention can be a random, block or segmented polymer. Preferably, the polymer is an absorbable random polymer. A polymer is "absorbable" within the meaning of this invention if it is capable of breaking down into small, non-toxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within twelve months, most preferably within six months.

The preferred random copolymers can be made using conventional polymerization techniques. The reactive components can be charged to a suitable polymerization vessel, and subjected to an elevated temperature for a sufficient period of time to form the polymer of desired viscosity. An initiator is unnecessary to initiate the polymerization, because the castor oil acts as an initiator. However, it may be desirable in some instances to employ convention initiators, e.g. dodecanol for certain applications.

The preferred random copolymers exhibit an inherent viscosity, as measured in at a concentration of 0.1 gram per deciliter (g/dl) in hexafluoroisopropanol (HFIP) at 25° C., between about 0.05 to about 2.0 dl/g, preferably about 0.10 to about 0.80 dl/g. If the inherent viscosity were less than about 0.05 dl/g, then the polymer may not have the integrity necessary for the preparation of films or coatings for the surfaces of various surgical and medical articles. On the other hand, although it is possible to use polymers with an inherent viscosity greater than about 2.0 dl/g, it may be exceedingly difficult to do so.

The polymers of this invention can be easily fabricated into numerous surgical articles. As this term is used, a surgical article is any article used in or for the diagnosis, monitoring, treatment or prevention of disease, sickness or other physical condition. The surgical article can be shaped to form any structure particularly adapted for a desired application. For example, the article can be in the form of a needle or suture. Alternatively, the article can exist in the form of tubular structures such as vascular prothesis, or as a film or membrane for numerous applications. The preferred articles are surgical sutures and needles. The most preferred article is a surgical needle. Preferably, the needle is attached to a surgical suture.

In the most preferred embodiment, the polymer is used to coat a surface of a surgical article to enhance the lubricity of the coated surface. The polymer may be applied as a coating using conventional techniques. For example, the polymer may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

Although it is contemplated that numerous surgical articles (including but not limited to endoscopic instruments) can be coated with the polymer of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, $\epsilon$-caprolactone, 1,4-dioxanone, and trimethylene carbonate. The preferred suture is a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 parts by weight. If the amount of coating on the suture were greater than about 30 weight percent, then it may increase the risk that the coating may flake off when the suture is passed through tissue.

Sutures coated with the polymers of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of this invention.

In another embodiment of the present invention when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

The following examples illustrate the preferred embodiments of this invention, and should not be interpreted to limit the scope of the claimed invention. For example, the polymer may be used for numerous applications, such as for the fabrication of surgical articles or devices, and the relative proportions of the reactive monomeric components can be varied significantly as well, depending on the particular application desired.

EXAMPLE 1

Copolymer of Caster Oil/ε-Caprolactone/Glycolide @ 11/80/9 Initial Parts by Weight A flame dried, 250 ml, round bottom single neck flask is charged with 10.0 gm USP grade castor oil, 72.0 gm (0.63 mole) of ε-caprolactone, 8.0 gm (0.07 mole) of glycolide, and 0.0707 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for about 24 hours. The copolymer has an inherent viscosity of 0.47 dl/g in hexafluoroisopropanol (HFIP) at 25° C. The copolymer has melting point of 36°41° C.

EXAMPLE 2

Copolymer of Castor Oil/ε-Caprolactone/Glycolide @20/72/8 Initial Parts by Weight A flame dried, 250 ml, round bottom single neck flask is charged with 20.0 gm USP grade castor oil, 72.0 gm (0.63 mole) of ε-caprolactone, 8.0 gm (0.069 mole) of glycolide, and 0.1059 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for about 16 hours. The copolymer has an inherent viscosity of 0.30 dl/g in hexafluoroisopropanol (HFIP) at 25° C. and at a concentration of 0.1 g/dl.

EXAMPLE 3

Copolymer of Castor Oil/Glycolide @ 50/50 Initial Parts by Weight

To a flame dried, mechanically stirred 250 ml round bottom flask, suitable for polycondensation reactions, is charged with 50.0 gm USP grade castor oil, 50.0 gm (0.43 mole) of glycolide, and 5.3 milligrams of dibutyltin oxide. After purging the reaction flask and venting with nitrogen, the reaction mixture is heated gradually to 160° C. under nitrogen and maintained at this temperature for about 24 hours. The reaction mixture is allowed to cool to room temperature. Under high vacuum (0.1 mm Hg), the reaction flask is heated gradually to 200° C. in about 4 hours, and maintained at 200° C. for about 12 hours. The resulting copolymer has an inherent viscosity of 0.10 dl/g in hexafluoroisopropanol (HFIP) at 25° C. and at a concentration of 0.1 g/dl.

EXAMPLE 4

Copolymer of Castor Oil/ε-Caprolactone/Glycolide @40/10/50 Initial Parts by Weight A flame dried, 250 ml, round bottom single neck flask, suitable for polycondensation, is charged with 40.0 gm USP grade castor oil, 10.0 gm (0.088 mole) of ε-caprolactone, 50.0 gm (0.431 mole) of glycolide, and 0.0786 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for about 24 hours, 4 hours at 220° C., and about 16 hours at 205°–210° C. The reaction mixture is allowed to cool to room temperature. Under high vacuum (0.1 mm Hg), the reaction flask is heated gradually to 160° C. in about 4 hours, and maintained at this temperature for about 16 hours. The resulting copolymer has an inherent viscosity of 0.11 dl/g in hexafluoroisopropanol (HFIP) at 25° C. and at a concentration of 0.1 g/dl.

EXAMPLE 5

Copolymer of Castor Oil/ε-Caprolactone/Glycolide @ 20/36/44 Initial Parts by Weight A flame dried, 250 ml, round bottom single neck flask is charged with 20.0 gm USP grade castor oil, 36.0 gm (0.315 mole) of ε-caprolactone, 44.0 gm (0.379 mole) of glycolide, and 0.1059 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for about 16 hours. The copolymer has an inherent viscosity of 0.24 dl/g in hexafluoroisopropanol (HFIP) at 25° C. and at a concentration of 0.1 g/dl.

EXAMPLE 6

Copolymer of Castor Oil/ε-Caprolactone/p-Dioxanone @ 11/80/9 Initial Parts by Weight A flame dried, 250 ml, round bottom single neck flask is charged with 10.0 gm USP grade castor oil, 72.0 gm (0.63 mole) of ε-caprolactone, 8.0 gm (0.08 mole) of p-dioxanone, and 0.0717 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for about 24 hours. The copolymer is dried under vacuum (0.1 mm Hg) at 80° C. for about 12 hours to remove any unreacted monomer. A weight loss of 0.2% is observed. The copolymer has an inherent viscosity of 0.44 dl/g in hexafluoroisopropanol (HFIP) at 25° C. The copolymer has melting point of 39°–45° C.

EXAMPLE 7

A 15 percent coating solution of each of the copolymers of Examples 1, 2 and 3 in toluene, and 9.6 percent coating solution of each of the examples 4 and 5 in 1,1,2-trichloroethane are prepared. A size 2/0 (USP standard) Vicryl ™ braided multifilament suture is coated with each coating solution using conventional laboratory coating equipment. The physical properties of the coated sutures are evaluated and the results are reported in the following tables and compared with an uncoated control:

TABLE 1

PHYSICAL PROPERTIES OF SUTURES COATED WITH COPOLYMERS

| Ex. # | Coating % add-on | Diameter (mils) | Straight (lbs) | Intrinsic (psi) | Knot (lbs) | Intrinsic (psi) | Elg (%) |
|---|---|---|---|---|---|---|---|
| Control | N/A | 13.16 | 15.61 | 114800 | 8.04 | 59100 | 15.61 |
| 1 | 3.8 | 13.40 | 14.79 | 104900 | 9.31 | 66000 | 18.70 |
| 2 | 3.3 | 12.24 | 12.53 | 106700 | 8.80 | 74900 | 15.27 |
| 3 | 3.4 | 12.92 | 14.88 | 113500 | 8.91 | 68000 | 18.33 |
| 4 | 3.2 | 12.78 | 15.30 | 119500 | 8.52 | 66500 | 19.15 |
| 5 | 3.6 | 12.56 | 14.91 | 120400 | 9.03 | 73000 | 18.71 |

TABLE 2
HANDLING PROPERTIES OF SUTURES COATED WITH COPOLYMERS

| Example | Wet knot Slide Test (a) (lbs) Ave./SD | Skin tissue Drag Test (b) (lbs) Ave./SD | Wet Knot Security (c) (# of throws to secure knot) |
|---|---|---|---|
| control | 7.8/0.37 | 303/24 | 4 |
| 1 | 0.61/0.53 | 180/5 | 6 |
| 2 | 0.62/0.28 | 197/36 | 6 |
| 3 | 6.08/1.86 | 224/21 | 5 |
| 4 | 4.41/1.02 | 237/9 | 5 |
| 5 | 3.53/0.60 | 269/36 | 5 |

(a) The suture knot slide test is a method for measuring the ability to slide a preknotted looped suture down into a deep wound into a locking position during tissue proximation. This knot slide capability is often enhanced by the application of a coating to the surface of the suture. Force required for knot slide down of prewet sutures with distilled water is measured using an Instron Tensile Tester and recording device.
(b) Tissue drag is a measure of the relative smoothness of the suture while passing through tissue, and is measured by using an Instron Tensile tester and recording device.
(c) The knot security test is a method to determine the minimum number of throws to secure a knot in a suture to prevent slippage of the suture knot. It is determined by using an Instron Tensile Tester with visual observation of the knot security and breakage of the knot without slippage during the testing. The number of throws are recorded for securing the knot.

The data from Tables 1 and 2 illustrates that the castor oil copolymers improve the wet knot slide down and reduce the tissue drag while maintaining comparable physical properties relative to the uncoated control. Surprisingly, these coating copolymers improved the knot tensile strength of the suture from 12 to 27% relative to the uncoated control.

EXAMPLE 8

Needle coating solutions of the copolymers of Examples 1 and 6 are prepared in organic solvents. The needles are dipped in the corresponding polymeric solutions and cured in an oven for 1-24 hours at 100°-200° C. The needles are then tested for penetration.

Needle penetration values are obtained using the following general procedure:

A penetration membrane material called POR-VAIR ™, 0.45 mm thick, which is a trademark of Porvair Limited, is used for needle penetration measurements. An average of ten penetration values per needle, and five needles per group are used. Taper point BV-130-5 needles from Ethicon, Inc. are used for testing.

Each curved needle is mounted in a fixture which rotates about the center of the needle's curvature at a constant angular velocity. The penetration membrane is orientated such that the needle penetrates the surface at a perpendicular angle. The penetration membrane is directly attached to a calibrated strain gage load cell.

The load cell, in conjunction with proper signal conditioning equipment, generates a voltage proportional to the force exerted on the load cell. This voltage is measured and recorded on a strip chart recorder. The result is a graphical waveform representing the penetration force of the needle as a function of penetration depth. Each waveform is analyzed to extract the maximum force required to achieve penetration. The maximum force required for a needle to penetrate the POR-VAIR membrane is taken as the penetration value. An average of ten penetration values of five needles are taken for each example.

The penetration values of the needles coated with castor oil copolymers and an uncoated control are summarized in Table 3.

TABLE 3
NEEDLE PENETRATION VALUES FOR COATED NEEDLES

| Examples of Coating Systems | Cure Time/Temp | Needle Penetration Values |
|---|---|---|
| Example 9 | | |
| 20.0% of Ext. 1 | 1 hr/120° C. | 25.5 gm. |
| 80.0% Acetone | | |
| Example 10 | | |
| 100 parts of Ex. 9 | 3 hr/150° C. | 20.6 gm. |
| 0.5 parts of | | |
| Castor Oil (USP) | | |
| Example 11 | | |
| 19.0% of Ex.1 | 22 hr/120° C. | 13.5 gm. |
| 80.2% Acetone | | |
| 0.8% Glycerol | | |
| Example 12 | | |
| 20.0% of Ex.6 | 24 hr/120° C. | 23.0 gm. |
| 80.0 Acetone | | |
| Control | | |
| No coating-bare needles | — | 42.6 gm. |

The results illustrated in Table 3 show significantly reduced penetration values for the coated needles of this invention relative to the penetration value exhibited for the uncoated control.

I claim:
1. A polymer consisting essentially of
   a) a first monomer from the group consisting ε-caprolactone, trimethylene carbonate, an ether lactone and combinations thereof;
   b) castor oil; and
   c) a second monomer selected from the group consisting of glycolide, lactide, 1,4-dioxanone and combinations thereof.
2. The polymer of claim 1 wherein the first monomer is ε-caprolactone and the second monomer is selected from the group consisting of glycolide, lactide and combinations thereof.
3. The polymer of claim 2 wherein the amount of ε-caprolactone is between about 10 to about 90 parts by weight.
4. The polymer of claim 3 wherein the amount of ε-caprolactone is between about 20 to about 80 parts by weight.
5. The polymer of claim 4 wherein the amount of castor oil is between about 5 to about 60 parts by weight.
6. The polymer of claim 6 wherein the amount of castor oil is between about 10 to about 50 parts by weight.
7. The polymer of claim 6 wherein additionally present in the polymer is glycerol.
8. The polymer of claim 7 wherein the amount of glycerol is between about 5 to about 30 parts by weight.
9. The polymer of claim 8 wherein the amount of glycerol is between about 5 to about 15 parts by weight.
10. The polymer of claim 9 wherein the polymer random polymer.
11. The polymer of claim 10 wherein the polymer has an inherent viscosity of between about 0.10 to about 0.20 dl/g determined at a concentration of 0.1 g/dl in hexafluoroisopropanol at 25° C.
12. The polymer of claim 11 wherein the polymer has an inherent viscosity of between about 0.10 to about 0.80 dl/g determined at a concentration of 0.1 g/dl in hexafluoroisopropanol at 25° C.

13. A suture wherein the outer surface thereof is coated with a polymer consisting essentially of
   a) a first monomer from the group consisting of ε-caprolactone trimethylene carbonate, are either lactone and combinations thereof;
   b) castor oil; and
   c) a second monomer selected from the group consisting of glycolide, lactide, 1,4-dioxanone and combinations thereof.

14. The suture of claim 13 wherein the amount of the polymer coated on the outer surface of the suture is between about 0.5 to about 30 weight percent.

15. The suture of claim 14 wherein the amount of the polymer coated on the outer surface of the suture is between about 1.0 to about 20 weight percent.

16. The suture of claim 14 wherein the suture is a synthetic absorbable suture composed of homopolymer or copolymers of lactone monomers selected from the group consisting of glycolide, lactide, ε-caprolactone, 1,4-dioxanone and trimethylene carbonate.

17. The suture of claim 15 wherein the suture is a synthetic absorbable, braided multifilament suture.

18. The suture of claim 16 wherein the suture is composed of polyglycolide or poly(glycolide-co-lactide).

19. A surgical article having a surface coated with a lubricating bioabsorbable copolymer comprising the reaction product of a predominant amount of a lactone monomer selected from the group consisting of δ-caprolactone, trimethylene carbonate, an ether lactone and combinations thereof; and castor oil in an amount effective to enhance the lubricity of said surface.

20. The article of claim 19 wherein the lactone monomer is selected from the group consisting of glycolide, lactide, 1,4-dioxanone, trimethylene carbonate, δ-valerolactone, ε-caprolactone, 1,4-dioxepan-2-one, 1,5-dioxepan-2-one and mixtures thereof.

21. The article of claim 20 wherein the lactone monomer is selected from the group consisting of ε-caprolactone, 1,4-dioxanone, trimethylene carbonate, glycolide, lactide and mixtures thereof.

22. The article of claim 21 wherein the lactone monomer is selected from the group consisting of ε-caprolactone, 1,4-dioxanone, glycolide, and mixtures thereof.

23. The article of claim 22 wherein the lactone monomer is a mixture of ε-caprolactone with either glycolide or 1,4-dioxanone.

24. The article of claim 23 wherein the weight ration of ε-caprolactone to either glycolide or 1,4-dioxanone is between about 10 to about 90 parts by weight.

25. The article of claim 24 wherein the weight ratio of ε-caprolactone to either glycolide or 1,4-dioxanone is between about 50 to about 85 parts by weight.

26. The article of claim 25 wherein the amount of the lactone monomer is between about 70 to about 90 parts by weight.

27. The article of claim 26 wherein the amount of the lactone monomer is between about 80 to about 90 parts by weight.

28. The article of claim 27 wherein the copolymer is random copolymer.

29. The article of claim 28 wherein the copolymer has an inherent viscosity of between about 0.05 to about 2.0 dl/g determined at a concentration of 0.1 g/dl in hexafluoroisopropanol at 25° C.

30. The article of claim 29 wherein the copolymer has an inherent viscosity of between about 0.10 to about 0.80 dl/g determined at a concentration of 0.1 g/dl in hexafluoroisopropanol at 25° C.

31. The article of claim 30 wherein additionally present in the absorbable copolymer is glycerol.

32. The article of claim 31 wherein the amount of glycerol is between about 0.5 to about 30 weight percent.

33. The article of claim 32 wherein the article is a surgical needle.

34. The needle of claim 33 wherein the amount of copolymer coated on the surface of the surgical needle is an amount which yields a coating thickness between about 2 to about 20 microns.

35. The needle of claim 34 wherein the coating thickness is between about 4 to about 8 microns.

36. The needle of claim 34 wherein the needle is attached to a suture.

* * * * *